(12) United States Patent
Bandyopadhyay et al.

(10) Patent No.: US 9,440,002 B2
(45) Date of Patent: Sep. 13, 2016

(54) MATERIALS WITH MODIFIED SURFACES AND METHODS OF MANUFACTURING

(75) Inventors: Amit Bandyopadhyay, Pullman, WA (US); Susmita Bose, Pullman, WA (US)

(73) Assignee: Washington State University, Pullman, WA (US)

( * ) Notice: Subject to any disclaimer, the term of this patent is extended or adjusted under 35 U.S.C. 154(b) by 138 days.

(21) Appl. No.: 14/006,941

(22) PCT Filed: Mar. 26, 2012

(86) PCT No.: PCT/US2012/030544
§ 371 (c)(1),
(2), (4) Date: Sep. 23, 2013

(87) PCT Pub. No.: WO2012/135107
PCT Pub. Date: Oct. 4, 2012

(65) Prior Publication Data
US 2014/0010856 A1  Jan. 9, 2014

Related U.S. Application Data

(60) Provisional application No. 61/470,970, filed on Apr. 1, 2011.

(51) Int. Cl.
| | |
|---|---|
| *A61F 2/00* | (2006.01) |
| *A61L 27/04* | (2006.01) |
| *A61L 27/30* | (2006.01) |
| *A61L 27/50* | (2006.01) |
| *A61L 31/16* | (2006.01) |

(52) U.S. Cl.
CPC ............ *A61L 27/04* (2013.01); *A61L 27/306* (2013.01); *A61L 27/50* (2013.01); *A61L 31/16* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 5,840,083 A | 11/1998 | Braach-Maksvytis | |
| 2001/0003007 A1 | 6/2001 | Chinn et al. | |
| 2006/0129050 A1 | 6/2006 | Martinson | |
| 2007/0207335 A1* | 9/2007 | Karandikar et al. | 428/560 |
| 2009/0093881 A1* | 4/2009 | Bandyopadhyay et al. | 623/16.11 |
| 2011/0014258 A1* | 1/2011 | Gan et al. | 424/409 |

FOREIGN PATENT DOCUMENTS

| | | |
|---|---|---|
| CA | 2748760 A1 | 7/2010 |
| EP | 0641224 B1 | 8/1998 |

OTHER PUBLICATIONS

Extended European Search Report issued in European Application No. 12764588.5, on Oct. 9, 2014, 6 pages.
International Search Report and Written Opinion issued Oct. 25, 2012, in International Application No. PCT/US2012/030544.
X. Pang et al., Electrodeposition of hydroxyapatite-silver-chitosan nanocomposite coatings, Surface & Coatings Technology 202 (2008), pp. 3815-3821.
Xu Bingshe et al., Study on the Heat Resistant Property of Ag/4A Antibacterial Agent, Journal of Biomedical Materials Research Part B: Applied Biomaterials, 2007, vol. 84B, pp. 394-399.

* cited by examiner

*Primary Examiner* — Susan Tran
(74) *Attorney, Agent, or Firm* — Liang IP, PLLC

(57) ABSTRACT

Various embodiments of surface-modified devices, components, and associated methods of manufacturing are described herein. In one embodiment, an implantable device suitable for being implanted in a patient includes an implantable material having a utile shape and a surface and a modification material deposited on at least a portion of the surface of the implantable material. The modification material has a release rate in an implantation environment in the patient. The modification material at the release rate is effective as bactericidal without being cytotoxic to the patient.

20 Claims, 4 Drawing Sheets

MATERIALS WITH MODIFIED SURFACES AND METHODS OF MANUFACTURING

CROSS-REFERENCE TO RELATED APPLICATION(S)

This application is a National Stage Application of PCT Application No. PCT/US2012/030544, filed Mar. 26, 2012, which claims priority to U.S. Provisional Application No. 61/470,970, filed on Apr. 1, 2011.

STATEMENT REGARDING FEDERALLY SPONSORED RESEARCH

This work was supported in part by the Office of Naval Research (N00014-01-05-0583) and by the National Science Foundation (CTS-0134476, CMMI 0728348). The government has certain rights in this work.

BACKGROUND

Bone and joint replacement materials are useful for treating a wide variety of musculoskeletal disorders. For example, replacement materials can be designed to restore both lost structure and function, particularly for load bearing applications. Bones in healthy conditions carry external joint and muscular loads by themselves. Following insertions of orthopedic screws and/or other implants, the natural bone in the treated region shares its load-carrying capacity with the implanted components. Thus, the same load that had been originally born by the bone itself is now carried by the 'composite' new structure.

DETAILED DESCRIPTION

Figure 1:
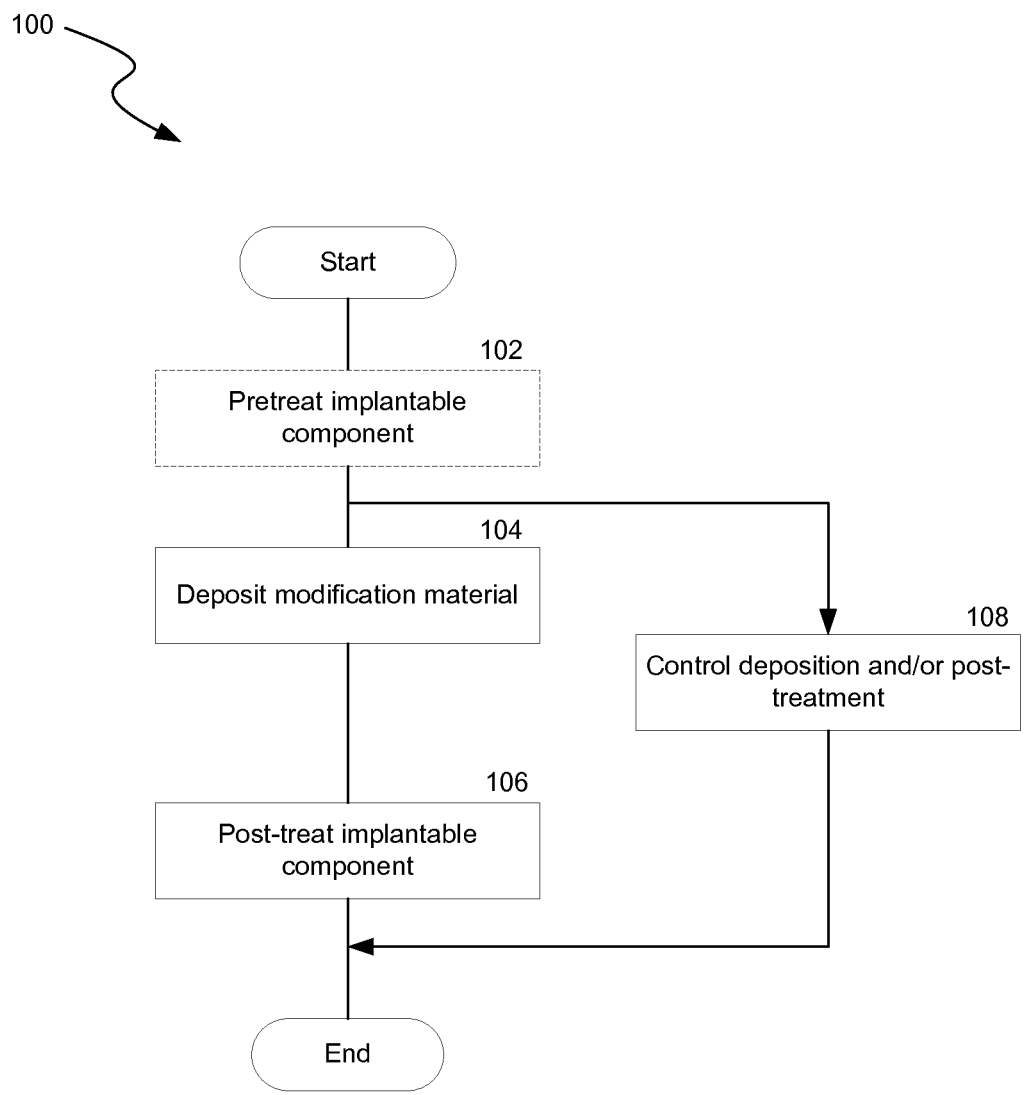
FIG. 1 is a flowchart illustrating a process of preparing an implantable component in accordance with embodiments of the technology.

Various embodiments of surface-modified devices, components, and associated methods of manufacturing are described below. Several embodiments of the disclosed surface-modified devices can improve interactions between implanted temporary or permanent bone replacement materials, and/or improve antimicrobial properties when compared to conventional metal implants. For example, it was discovered that surface modification of stainless steel ("SS") materials could negatively influence colonization of bacteria as well as promote interaction between human osteoblast cells and the modified implantable material. In the certain embodiments, silver (Ag) can be affixed on a surface of a structure to promote antimicrobial properties such as resistance to growth of Gram-negative bacteria (e.g., *Pseudomonas aeruginosa*). In other embodiments, gold, zinc oxide, copper, other metals, metal alloys with antimicrobial properties, and/or a combination thereof may also be used.

It will be appreciated that several of the details set forth below are provided to describe the following embodiment in a manner sufficient to enable a person skilled in the relevant art to make and use the disclosed embodiment. Several of the details and advantages described below, however, may not be necessary to practice certain embodiments of the disclosure. Additionally, the disclosure can include other embodiments that are within the scope of the claims but are not described in detail with respect to FIGS. 1-4.

It is believed that requirements for orthopedic metallic implants include (1) biocompatibility between an implant material and surrounding environment with little or no adverse cytotoxicity and tissue reaction; and (2) the implant material has mechanical and physical properties necessary to achieve the desired biophysical function. Some desired properties include, for example, low modulus, high strength, good ductility, good corrosion resistance in a body fluid medium, high fatigue strength, and good wear resistance.

An implantation challenge can occur when a metallic implant material is significantly stiffer than an adjacent bone. Internal load bearing functionality naturally performed by the bone can now be mainly supported by implanted screws or other structural implants. In some instances, such stress "shielding" of the natural bone can alter the normal stress stimuli for bone growth. The reduction of bone stress relative to a natural level causes the bone to adapt by reducing its mass in a process of resorption around the metallic implant material. This resorption/bone loss may cause possible loosening of the screw/implant and subsequent micro-motions of inserted screws/implants in response to external loads resulting in further damage to the interfacing bone and anchorage performances.

Infection can be a possible side effect often associated with implants and bone replacement surgeries. Infections, in some cases, may require removal of a surgically administered implant or cause a significant delay in post-surgical healing. This is often due to the accumulation of microbial plaque or biofilm development on implants, screws or plates, which can contribute to recurrent infections as well as cause bone loss or prevent the necessary natural bone deposition for anchoring the surgical implant. For temporary implants, e.g. SS rods and nails, selection and application of surface materials may enhance biocompatibility and increase antimicrobial nature of the implant than without such surface materials.

By depositing a surface material that is both biocompatible and antimicrobial onto an implant, the foregoing surgical and/or post-surgical difficulties may be lessened or prevented completely. Silver (Ag) is one surface material that has antimicrobial properties. However, when silver is available to the surrounding tissue, silver can then have an antimicrobial effect. Thus, bioavailable silver may not be permanently adhered to the surface of the implant. Conversely, silver that detaches from the surface of the implant too rapidly may poison the host. Therefore, certain rates of diffusion from the surface of the implant to the tissue adjacent the implant may be selected for safe treatment of the patient. As a result, silver ions may be released into the surrounding tissue in a concentration high enough to be bactericidal without becoming cytotoxic to the tissue.

As described with respect to the particular embodiments below, by first electrodepositing silver onto an implant and then annealing the electroplated implant, diffusion rates of silver ions from a surface of the implant into surrounding tissues of a body can be controlled or adjusted. For example, altering duration and temperature of the annealing process can achieve different diffusion rates. This process may be applied to silver and/or the other surface metals discussed herein.

Several embodiments of the technology are directed to methods for producing both permanent and temporary bone replacement materials and components with improved antimicrobial properties. Surface modifications to enhance interactions between bone cells and implant materials, e.g., SS based and/or other suitable materials are described herein. Some embodiments comprise surface coatings for SS metal implants using electrochemical processing and/or other surface modification techniques to enhance bone cell-materials interactions and achieve improved antimicrobial properties. In certain embodiments, the surface treatment methods described herein can be applied as a post-processing operation to metallic implants such as hip, knee, and spinal devices (e.g., screws, pins and plates). In other embodiments, the surface treatment methods can also be applied in other suitable processing operations to other types of implants.

FIG. 1 is a flowchart illustrating a process 100 of preparing an implantable component in accordance with embodiments of the technology. As shown in FIG. 1, the process 100 can include an optional stage 102 in which the implantable component is pretreated. In certain embodiments, the implantable component can include a screw, a pin, a rod, a plate, and/or other suitable structural component constructed from an implant material. Examples of implant material can include:
- a metal (e.g., titanium (commercially pure Ti, and both α and β alloys); aluminum (Al), iron (Fe), vanadium (V), etc.);
- a metal alloy (e.g., Ti alloys with major alloying elements such as Al, V, Nb, Fe, Zr, Mo, O, Ni, Cr, Co; Ta forming alloys such as Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; stainless steel, CoCrMO, etc.)
- a metal oxide (e.g., TiO2)
- ceramic (e.g., calcium aluminate, calcium hydroxyapatite and tricalcium phosphate)
- an inorganic salt (e.g., various forms of calcium phosphates and calcium carbonates and their combinations)
- a polymeric material (e.g., PMMA (poly-methyl-methacrylate), PHEMA (poly-hydroxyl-ethyl-methacrylate), and HTR (calcium hydroxide))

In other examples, the implant material can also include other suitable materials and/or a combination of at least some of the foregoing materials.

In certain embodiments, pretreating the implantable component can include cleaning, washing, bathing, sanding, and/or otherwise treating the implantable component. In other embodiments, pretreating the implantable component can include chemically activating a surface of the implantable component by removing oxides and/or other passivation materials from the surface of the implantable component. In further embodiments, the implantable component may be pretreated with other suitable techniques.

The process 100 then includes depositing a modification material onto the surface of the implantable component at stage 104. In certain embodiments, the deposited modification material can be "spotty" (e.g., with a surface area coverage of about 0.1% to about 10%) on the surface of the implantable component. In other embodiments, the deposited modification material can have a surface area coverage of about 0.1% to about 50%. In further embodiments, the deposited modification material can have other suitable surface area coverage values.

In one embodiment, the surface (e.g., a SS surface) of the implantable component is modified by electrolytic deposition to deposit silver (Ag) onto the SS surface. Ag coated surfaces, in accordance with aspects of the technology, are shown to have antimicrobial properties. For example, a modified or non-modified SS surface having a silver electroplated coating can effectively inhibit greater than 99% of *Pseudomonas aeruginosa* colony growth. Non-modified or modified SS substrate surfaces without silver deposition are not believed to have these inhibitory properties against colony formation and growth of *P. aeruginosa*. In other embodiments, the modification material may include gold, zinc oxide, copper, and/or other suitable compositions deposited onto the surface of the implantable component by sputtering, chemical vapor deposition, atomic layer deposition, and/or other suitable deposition techniques.

Moreover, depositing the modification material can also include performing surface modifications and/or combinations of surface modifications in a target pattern. For example, a surface modification may include forming a surface pattern (e.g., circles, squares, honeycombs, weaves, etc.) on the implantable component. In another example, a surface modification can include forming a layered and/or interleaved structure on the implant. Furthermore, the surface modification described herein can be combined with other suitable modifications used in the relevant art.

The process 100 can then include post-treating the implantable component with the deposited modification material at stage 106. In one embodiment, post-treating the implantable component can include annealing the implantable component at an annealing temperature for an annealing duration. In other embodiments, post-treating the implantable component can include case hardening, precipitation strengthening, tempering, quenching, and/or other suitable heat treatments. In further embodiments, post-treating the implantable component can also include chemical modification, machining, and/or other suitable chemical and/or physical operations.

In at least some of the foregoing embodiments, the deposition and/or post-treating operations do not substantially affect a mechanical property (e.g., tensile strength, compressive strength, yield strength, Young's modulus, ductility, toughness, etc.) of the implantable component. For example, at least one of the foregoing mechanical properties of the implantable component may stay generally constant after the deposition and/or post-treating operations. In other examples, at least one of the foregoing mechanical properties may vary at most by about ±1%, about ±5%, about ±10%, and/or other suitable values.

In addition, the deposition and/or post-treating operations can result in a strong adhesion of the deposited modification material (e.g., silver) to the surface of the implantable component such that simple touching does not dislodge the deposited material from the surface. For example, the deposited modification material (e.g., silver) can have an interfacial shear strength of about 10 MPa. In other examples, the deposited modification material (e.g., silver) can have an interfacial shear strength of about 1 MPa to about 30 MPa, or other suitable values.

As shown in FIG. 1, the process 100 can further include controlling deposition of the modification material and/or post-treatment of the implantable component based on a target release rate of the modification material in an implantation environment at stage 108. For example, in one embodiment, the modification material is deposited via electrolytic deposition. Thus, controlling deposition can include adjusting at least one of (1) a concentration of ion of the modification material in an electrolyte solution, (2) a potential applied during deposition, (3) a deposition period, (4) a deposition temperature, and/or other suitable process conditions. In another embodiment, the post-treatment includes annealing the implantable component. Thus, controlling the post-treatment can include adjusting an annealing temperature, an annealing duration, a heat up/cool down rate, an annealing atmosphere, and/or other suitable annealing parameters. In further embodiments, other suitable deposition and/or post-treatment parameters may also be adjusted based on a target release rate of the modification material in an implantation environment. In certain embodiments, a concentration of the released modification material can be from about 0.01 mg/L to about 30 mg/L. In other embodiments, the concentration can have other suitable values.

Embodiments of the process 100 can be used to modify implantable components having any size and shape. Furthermore, some embodiments of the process 100 for modifying may include modifying only a portion of the surface of the implantable component. Furthermore, the implantable component may include a first modified surface having a first modification, a second modified portion having a second modification, and a third modified portion having a third modification, and/or other modified portions with similar or different modifications. While sample sizes, shapes, and forms of implantable metal are disclosed herein, one of ordinary skill in the art will recognize other sizes, shapes and forms of samples that can be used as examples and/or as implantable devices. In further embodiments, an implantable material may be processed according to several embodiments of the process 100 and subsequently formed into a utile shape for particular implantation applications.

Figure 2A:
FIG. 2A is a photo depicting an x-ray image of a pre-operation leg fracture.
Figure 2B:
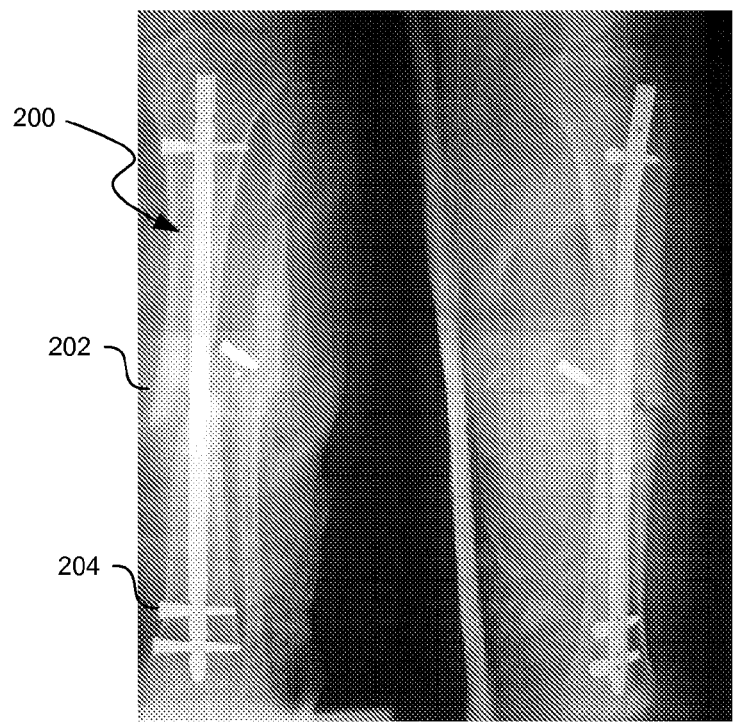
FIG. 2B is a photo depicting an x-ray image of a post-operation leg fracture with an implanted nail-and-rod assembly prepared in accordance with embodiments of the technology.

FIG. 2A is a photo depicting an x-ray image of a pre-operation leg fracture, and FIG. 2B is a photo depicting an x-ray image of a post-operation leg fracture with an implanted nail-and-rod assembly 200 prepared in accordance with embodiments of the process 100. As shown in FIGS. 2A-2B, the nail-and-rod assembly 200 can be inserted into tissues surrounding a fractured bone 202. The assembly 200 is attached to the bone 202 to enhance union of the fractured bone fragments. The rod-and-nail assembly 200 can be made of a suitable implant material, such as SS, having surface modifications for improving bone cell-materials interactions and/or inhibiting bacterial growth for reducing risks related to post-surgical infection. In one embodiment, at least the stem portion 204 can have single surface modification (e.g., electroplated silver). In other embodiments, at least the stem portion 204 may include a combination of silver deposition and/or other metal coatings.

EXAMPLES

The following examples are intended to demonstrate one embodiment of the technology more fully without limiting the scope of the disclosure, as numerous modifications and variations can be apparent to those skilled in the relevant art. In the following described examples, the surface of an implantable component of stainless steel was modified to enhance interactions between bone cells and the metal implantable materials as well as to increase antimicrobial properties for improving post-surgical healing and reducing the risk of postoperative infection.

Silver (Ag) was electrically deposited onto a surface of an SS substrate. By adjusting at least one of (1) a concentration of Ag ions in a solution, (2) a potential applied to the system to affect deposition, (3) a period in which the deposition occurs, and/or other suitable process conditions, various thicknesses of silver were deposited onto the SS surface. Samples of the SS substrate were exposed to a 0.1M solution of silver nitrate, and a current was applied for approximately two and a half minutes. After the treatment, silver could be visually seen on the surface of the SS substrate.

To be useful as a medical treatment device, it is believed that a Minimum Inhibitory Concentration (MIC) is required for the silver to be fully effective. However, too high of a concentration can be cytotoxic and cause human cell death. It is believed that MIC varies for each bacterium, but a general concentration range for inhibition is believed to be about 0.5 to about 10 mg/L. For bactericidal effectiveness, a minimum concentration of 2-20 mg/L is believed to be effective. The concentration of silver released into the surrounding tissue may be chosen based on particular treatment circumstances (e.g., physiological characteristics of a patient, target bacteria, etc.). Concentrations higher than 10 mg/L are believed to have a higher probability of being toxic to human cells.

Figure 3:
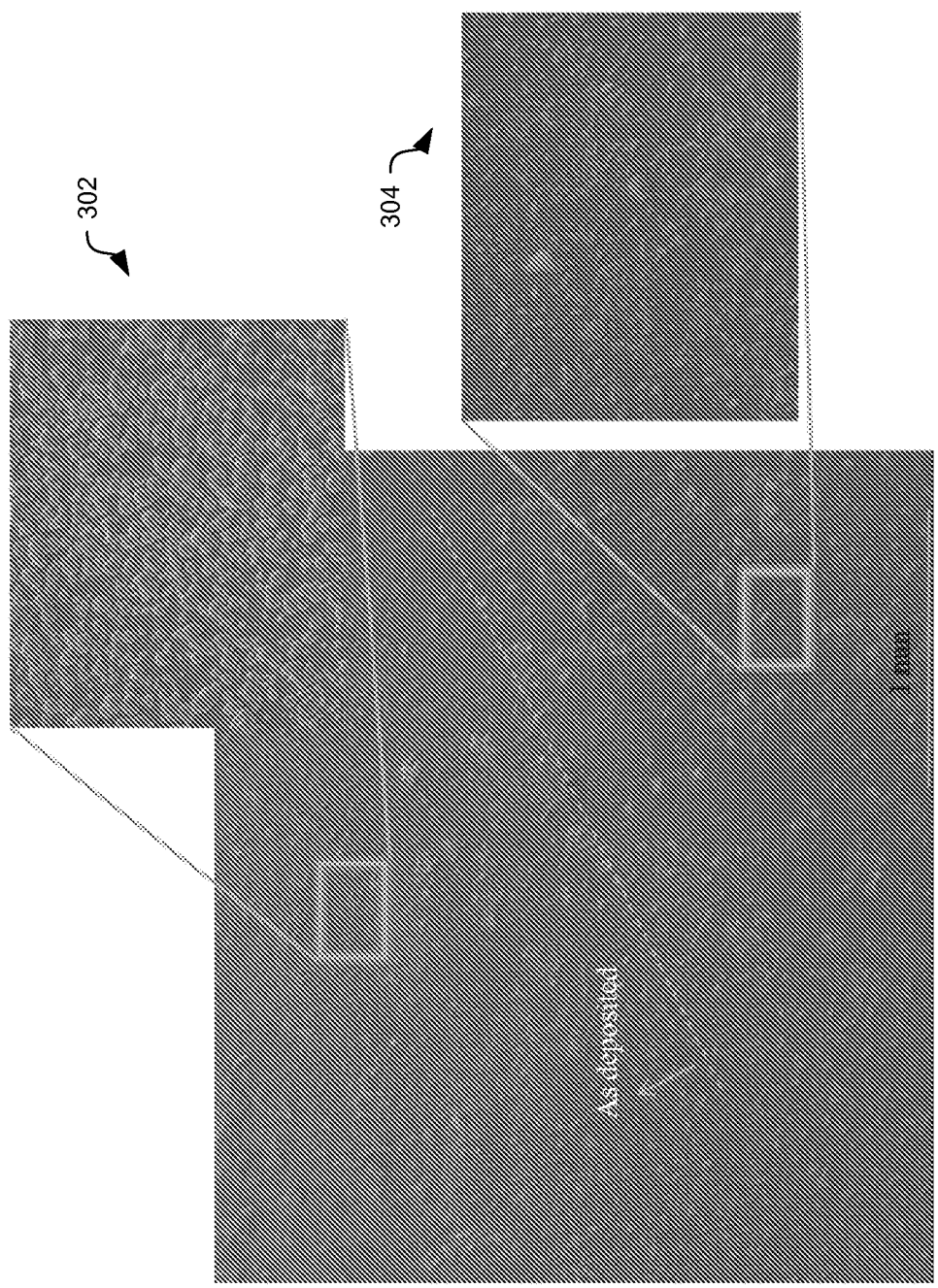
FIG. 3 depicts a scanning electron microscope ("SEM") image of a sample having heat-treated, electrolysis-deposited silver on stainless steel in accordance with embodiments of the technology.

The SS substrate, after silver electrolytic deposition, was baked between about 400 and about 500 degrees Celsius for 3-10 minutes to produce an implant device with an electroplated silver surface that can diffuse into the body to be bactericidal without becoming cytotoxic. FIG. 3 depicts an image of an SS substrate sample that was baked at 500 degrees Celsius for 8 minutes. The upper image 302 in FIG. 3 shows the sample after baking. The lower image 304 shows the baked sample subjected to a "tape test" in which an adhesive surface is pressed against the electrolytic deposited surface and then removed. Some of the deposited silver is released onto the adhesive surface. The amount of silver released is believed to vary with the ion concentration and current in the electrolytic deposition process and to be affected by changes in baking temperature and baking duration. Other suitable baking temperatures can include about 200° C. to about 700° C.

Figure 4:
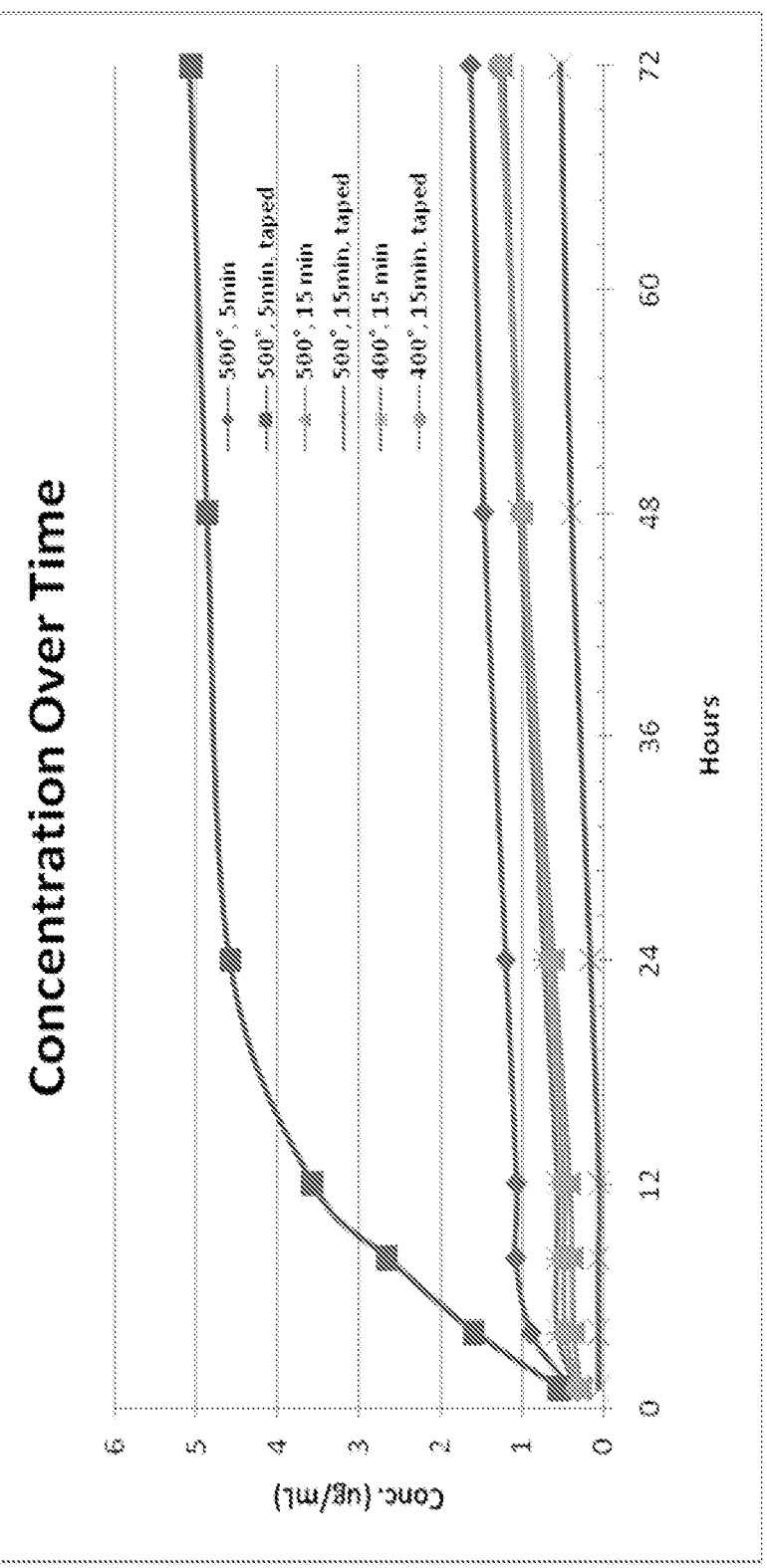
FIG. 4 is a graphical representation depicting a concentration of silver ions released into a solution of simulated human body fluid over time in accordance with embodiments of the technology.

The prepared sample was then put in contact with a simulated human body fluid and concentration of the silver ions was recorded over time. FIG. 4 is a graphical depiction showing a concentration of silver ions in simulated human body fluid conditions as a function of time. The chart indicates that the silver-coated implant exhibits continuous antimicrobial activity over long period.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:
1. A method for preparing an implantable device, comprising:
 depositing a modification material onto at least a portion of a surface of an implantable device;
 post treating the implantable device with the deposited modification material, wherein post treating the implantable device includes annealing the implantable device at an annealing temperature for an annealing duration; and controlling at least one process condition during post treating the implantable device with the deposited modification material based on a target release rate of the deposited modification material into human tissue in an implantation environment, wherein controlling the at least one process condition includes controlling at least one of the annealing temperature or the annealing duration, wherein:

the modification material includes silver;

the implantable device includes a stainless steel surface;

depositing the modification material includes depositing silver onto at least a portion of the stainless steel surface of the implantable device via electrolytic deposition, the deposited silver having a surface area coverage of about 0.1% to about 50%;

post treating the implantable device includes annealing the implantable device with the deposited silver without substantially affect a mechanical property of the implantable device with the stainless steel surface, the mechanical property including one of tensile strength, compressive strength, yield strength, Young's modulus, ductility, and toughness, wherein the deposited and post treated silver has an interfacial shear strength of about 1 MPa to about 30 MPa; and the method further includes controlling at least one process condition when depositing the modification material by adjusting at least one of:
   a concentration of silver and/or ions thereof in an electrolyte solution,
   an electrical deposition potential,
   a deposition temperature,
   a deposition period,
   a heat up rate, or
   a cool down rate based on a target release rate corresponding to a concentration of the modification material of about 0.5 to about 10 mg/L in the implantation environment.

2. The method of claim 1 wherein the modification material includes at least one of gold, zinc oxide, or copper in addition to silver.

3. The method of claim 1, further comprising selecting the target release rate based on (1) an effective inhibition concentration of the modification material in the implantation environment and (2) a threshold concentration at which the modification material is cytotoxic.

4. The method of claim 1 wherein:

the modification material is a first modification material; and the method further includes depositing a second modification material onto at least a portion of the surface of the implantable device and forming a layered and/or interleaved structure on the at least a portion of the surface.

5. The method of claim 1 wherein:

the modification material is a first modification material;

the at least a portion of the surface is a first surface portion; and the method further includes depositing a second modification material onto a second surface portion of the implantable device.

6. A method for preparing an implantable device, comprising:

selecting a target release rate of a modification material based on an implantation environment, the modification material at the target release rate being effective as a bactericidal without being cytotoxic;

forming a modification region on at least a portion of a surface of an implantable material, the modification region having the modification material; and adjusting at least one process condition when forming the modification region on at least a portion of the surface of the implantable material based on the selected target release rate of the modification material into the implantation environment, wherein:

the modification material includes silver;

the implantable device includes a stainless steel surface;

forming the modification region includes depositing silver onto at least a portion of the stainless steel surface of the implantable device via electrolytic deposition, the deposited silver having a surface area coverage of about 0.1% to about 50%;

the method further includes post treating the implantable device by annealing the implantable device with the deposited silver without substantially affect a mechanical property of the implantable device with the stainless steel surface, the mechanical property including one of tensile strength, compressive strength, yield strength, Young's modulus, ductility, and toughness, wherein the deposited and post treated silver has an interfacial shear strength of about 1 MPa to about 30 MPa; and adjusting at least one process condition includes adjusting at least one of:
   a concentration of silver and/or ions thereof in an electrolyte solution,
   an electrical deposition potential,
   a deposition temperature,
   a deposition period,
   a heat up rate, or
   a cool down rate based on a target release rate corresponding to a concentration of the modification material of about 0.5 to about 10 mg/L in the implantation environment.

7. The method of claim 6 wherein selecting the target release rate includes selecting the target release rate based on at least one of a physiological characteristic of a patient to receive the implantable device and a target bacterium to inhibit.

8. The method of claim 6 wherein selecting the target release rate includes selecting the target release rate to correspond to a concentration of the modification material of about 0.5 to about 10 mg/L in the implantation environment.

9. The method of claim 6 wherein selecting the target release rate includes selecting the target release rate to correspond to a concentration of the modification material of about 0.01 to about 30 mg/L in the implantation environment.

10. The method of claim 6 wherein selecting the target release rate includes selecting a target release rate of at least one of silver, gold, zinc oxide, and copper based on an implantation environment.

11. The method of claim 6 wherein forming the modification region includes:

electrochemically depositing particulates of at least one of gold, zinc oxide, or copper in addition to silver on at least a portion of the surface of the implantable material; and heating the implantable material with the deposited particulates to about 200° C. to about 700° C.

12. A method for preparing an implantable device, comprising:

depositing a modification material containing silver onto at least a portion of a stainless steel surface of the implantable device via electrolytic deposition, the deposited silver having a surface area coverage of about 0.1% to about 50%;

annealing the implantable device with the deposited silver without substantially affect a mechanical property of the implantable device with the stainless steel surface, the mechanical property including one of tensile strength, compressive strength, yield strength, Young's modulus, ductility, and toughness, wherein the deposited and annealed silver has an interfacial shear strength of about 1 MPa to about 30 MPa;

controlling at least one process condition during deposition of the modification material by adjusting at least one of:

a concentration of silver and/or ions thereof in an electrolyte solution, an electrical deposition potential, a deposition temperature, a deposition period, a heat up rate, or a cool down rate based on a target release rate corresponding to a concentration of the modification material of about 0.5 to about 10 mg/L in the implantation environment; and controlling at least one process condition during annealing the implantable device with the deposited modification material based on a target release rate of the deposited modification material into human tissue in an implantation environment, wherein controlling the at least one process condition includes controlling at least one of the annealing temperature or the annealing duration.

13. The method of claim 12 wherein:

the modification material is a first modification material; and the method further includes depositing a second modification material onto at least a portion of the surface of the implantable device and forming a layered and/or interleaved structure on the at least a portion of the surface.

14. The method of claim 12 wherein:

the modification material is a first modification material;

the at least a portion of the surface is a first surface portion; and the method further includes depositing a second modification material onto a second surface portion of the implantable device.

15. The method of claim 12, further comprising selecting the target release rate based on (1) an effective inhibition concentration of the modification material in the implantation environment and (2) a threshold concentration at which the modification material is cytotoxic.

16. The method of claim 12, further comprising selecting the target release rate based on an implantation environment, the modification material at the target release rate being effective as a bactericidal without being cytotoxic.

17. The method of claim 16 wherein selecting the target release rate includes selecting the target release rate based on at least one of a physiological characteristic of a patient to receive the implantable device and a target bacterium to inhibit.

18. The method of claim 16 wherein selecting the target release rate includes selecting the target release rate to correspond to a concentration of the modification material of about 0.5 to about 10 mg/L in the implantation environment.

19. The method of claim 16 wherein selecting the target release rate includes selecting the target release rate to correspond to a concentration of the modification material of about 0.01 to about 30 mg/L in the implantation environment.

20. The method of claim 16 wherein forming the modification region includes:

electrochemically depositing particulates of at least one of gold, zinc oxide, or copper in addition to silver on at least a portion of the surface of the implantable material; and heating the implantable material with the deposited particulates to about 200° C. to about 700° C.

* * * * *